United States Patent [19]

Steer

[11] Patent Number: 4,973,324
[45] Date of Patent: Nov. 27, 1990

[54] OSTOMY COUPLING

[75] Inventor: Peter L. Steer, East Grinstead, England

[73] Assignee: E. R. Squibb & Sons, Inc., Princeton, N.J.

[21] Appl. No.: 320,009

[22] Filed: Mar. 6, 1989

[30] Foreign Application Priority Data

Mar. 23, 1988 [GB] United Kingdom ............... 8806933

[51] Int. Cl.$^5$ ............................................. A61F 5/44
[52] U.S. Cl. ................................................ 604/342
[58] Field of Search ........ 604/277, 317, 327, 332–345; 285/200, 364, 365, 406, 407

[56] References Cited

U.S. PATENT DOCUMENTS

| 3,736,934 | 6/1973 | Hennessy . | |
|---|---|---|---|
| 4,460,363 | 7/1984 | Steer et al. | 604/336 |
| 4,642,107 | 2/1987 | Arnone et al. | 604/342 |
| 4,834,732 | 5/1988 | Steer et al. | 604/342 |

FOREIGN PATENT DOCUMENTS

| 0135269 | 3/1985 | European Pat. Off. . |
| 3417183 | 5/1984 | Fed. Rep. of Germany . |
| 802823 | 9/1936 | France . |
| 8503427 | 8/1986 | PCT Int'l Appl. . |
| 1021145 | 3/1966 | United Kingdom . |
| 1099455 | 1/1968 | United Kingdom . |
| 1568860 | 6/1980 | United Kingdom . |
| 1579875 | 11/1980 | United Kingdom . |
| 2121902 | 3/1982 | United Kingdom . |
| 2177926 | 2/1987 | United Kingdom . |
| 2183481 | 6/1987 | United Kingdom . |
| 2193098 | 2/1988 | United Kingdom . |
| 2201345 | 9/1988 | United Kingdom . |
| 2201346 | 9/1988 | United Kingdom . |
| 2205041 | 11/1988 | United Kingdom . |

Primary Examiner—John D. Yasko
Assistant Examiner—Anthony M. Gutowski
Attorney, Agent, or Firm—Stephen B. Davis

[57] ABSTRACT

An ostomy coupling has a first channel shaped element for attachment to an ostomy bag and a second element for attachment to a pad of medical grade adhesive. Each of these elements surrounds a stomal orifice. The second element is made into parts. The first attaches to the pad and the second is slidable axially relative to the first part. Moreover, the second part has a flange under which fingers can be placed when joining the elements to substantially prevent the application of pressure to the peristomal area.

8 Claims, 3 Drawing Sheets

OSTOMY COUPLING

BACKGROUND OF THE INVENTION

This invention relates to an ostomy coupling. Such couplings are used to attach an ostomy bag to a person who is obliged to wear such a bag as a result of a surgical operation such as colostomy, ileostomy or urostomy.

It is customary nowadays for a pad of medical grade adhesive to be applied to the skin area surrounding the stoma. To this pad is attached one coupling element and a counterpart coupling element is attached to the ostomy bag. One example of a successful system of this kind can be seen in British Patent Nos. 1 571 657 and 1 568 860. It is desirable that the coupling is such that it is secure when attached, but can be coupled and uncoupled using a relatively small axial force. Pressure must be applied to the stomal area when coupling the elements together and this often causes pain because the peristomal area is tender and sensitive. Efforts have been made, e.g. in U.K. Patent No. 2 115 288 and in European Patent Application No. 98718 to provide a coupling arrangement which allows the wearer to absorb some of the pressure when attaching coupling elements to each other by placing his/her fingers behind a portion of the coupling. For various reasons these efforts have not been entirely successful.

SUMMARY OF THE INVENTION

According to the present invention, there is provided an ostomy coupling which includes a first channel shaped element for attaching to an ostomy bag and a second element for attaching to a pad of medical grade adhesive, each of these elements surrounding a stomal orifice, in which the second element comprises a first part for attaching to the pad and a second part which is axially slidable relative to the first part and which has a radially outer external flange under which the fingers can be placed when joining the elements to substantially prevent the application of pressure to the peristomal area.

The second part is preferably shaped so that when at the limit of its axial travel away from the pad, it co-operates with a stop on the first part to define a portion of the second coupling element shape chosen to be complementary to the first coupling element.

Optionally, the second part may include or may have attached thereto a pair of belt lugs.

The first part preferably includes a chute member for surrounding the stomal orifice. The chute member preferably has a peripheral flexible seal strip located internally of the end of the chute which is remote from the pad. The chute member is preferably substantially cylindrical.

The second part preferably includes a ring portion and a flange portion extending radially outwardly therefrom. The ring portion preferably has a peripheral recess therein shaped for receiving a rim portion of the first part, when the first part is at its aforesaid limit of travel.

The coupling described and illustrated herein is particularly suitable for loop ostomy use. As the skilled man will be aware, in loop ostomy bags it is particularly important to be able to couple and uncouple the bag from the patient without applying pressure to the abdomen.

The invention will be better understood from the following illustrative and non-limiting description of one embodiment thereof, given with reference to the accompanying drawings in which like parts are represented by like reference numerals and in which:

Figure 1:
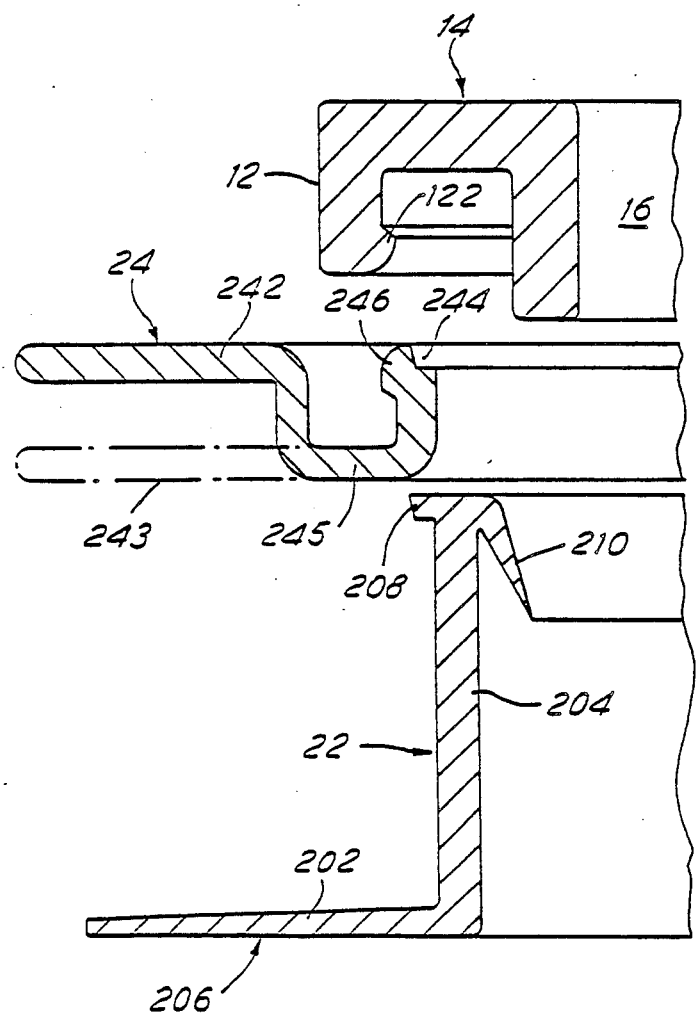
FIG. 1 is a cross-sectional view taken in an axial plane of one embodiment of ostomy coupling, showing the parts separated.
Figure 2:
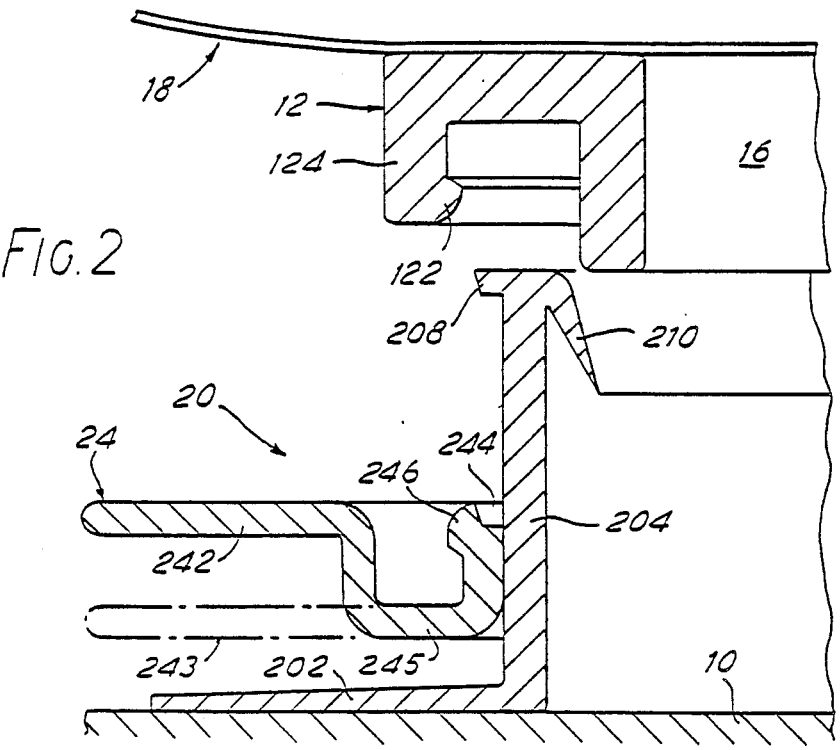
FIG. 2 is a view as in FIG. 1 showing the two parts of the second coupling element assembled together.
Figure 3:
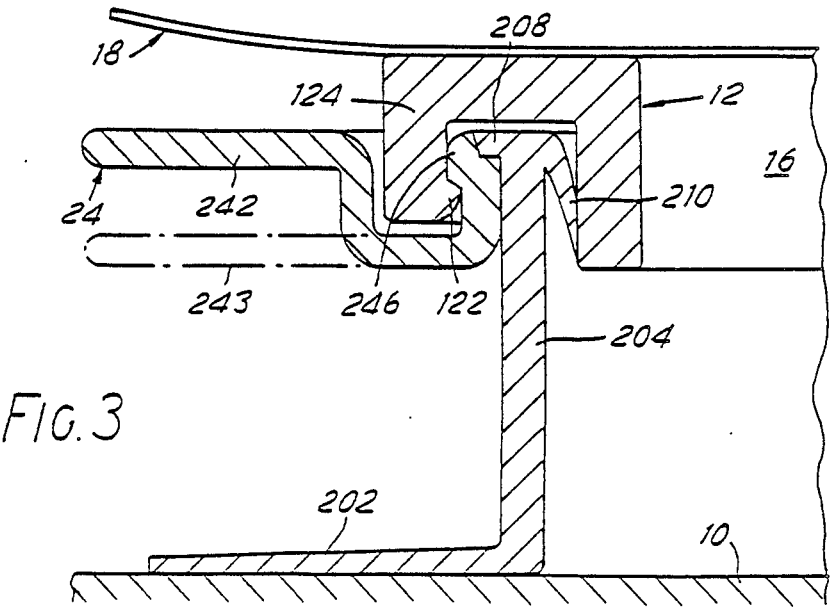
FIG. 3 is a view similar to FIG. 1 showing the ostomy coupling in a coupled condition.
Figure 4:
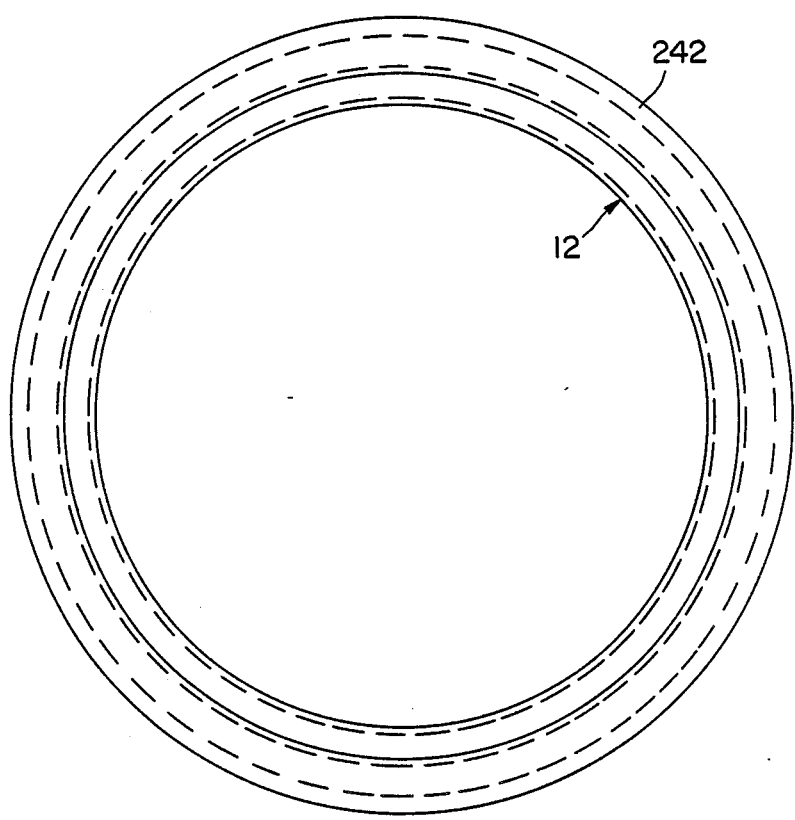
FIG. 4 is a front elevation of the coupling of FIGS. 1–3, but omitting the belt lugs.
Figure 5:
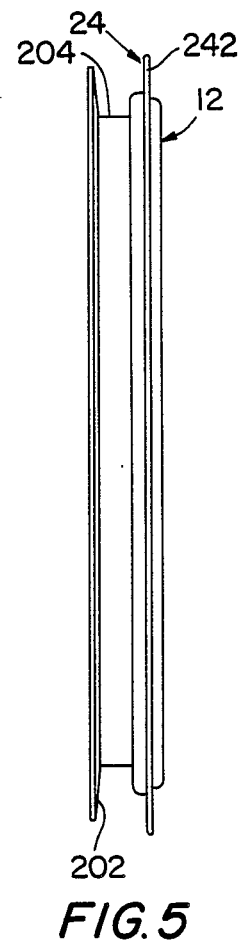
FIG. 5 is a side view of the assembled coupling on the same scale as FIG. 4.

For simplicity of illustration, in the sectional views of FIGS. 1–3, only one side of the coupling is shown. It will be understood that the coupling is of closed loop form and is intended to surround the stoma of the wearer. It is attached to the peristomal area of the body of the wearer in conventional manner by a pad of medical grade adhesive seen at 10 in FIG. 2.

The illustrated ostomy coupling is of substantially circular form but of course could be oval or any other convenient shape to surround the stoma. For brevity of description, a circular coupling is particularly described herein but the invention is not regarded as limited to circular/annular couplings.

The illustrated ostomy coupling includes a first annular channel shaped coupling element for attachment to an ostomy bag. The element 12 has a surface 14 to which one wall of the bag, having a stomal orifice 16, is attached in any convenient manner. The channel shaped coupling element may be constructed in accordance with the teaching in British Patent Nos. 1 571 657 and 1 568 860. In FIG. 2 the bag wall, which is the bag rear wall as worn, is seen at 18.

The second coupling element 20 is designed for inter-engaging co-operation with the first coupling element 12 and includes a first part 22 and a second part 24.

The first part 22 may be made as a single molding of EVA synthetic plastics material. It includes a flange 202 and a substantially cylindrical chute member 204. The flange 202 has a surface 206 by which the flange may be attached by heat welding or adhesive or other suitable manner to the medical grade adhesive pad 10. The chute member 204 encircles the stoma of the wearer, an has, at its end remote from the flange 202, a radially outwardly projecting rim 208 and an inwardly extending flexible and deflectable seal strip 210. The seal strip 210 is constructed in accordance with the teachings in British Patent No. 1 568 860.

The second part 24 of the second coupling element is generally annular in form and may be made as a single molding of a polyester synthetic plastics material. It has an outwardly extending flange 242 and a recess 244 which is designed to snuggly receive the rim 208. The part 24 is, in use, sprung over the chute member 204 and can slide in an axial direction thereon. The assembled condition of these parts is seen in FIG. 2. The part 24 is axially slidable relative to the chute member 204 of the part 22 and, adjacent the recess 244, there is provided a radially outwardly extending rim 246 whose chief purpose is to co-operate with an inwardly extending rim 122 on the radially outer wall 124 of the coupling element 12.

Assuming that the medical adhesive pad is attached to the peristomal area of a user, when the user wishes to attach the pouch, he (or she) lifts the part 24 away from the body by placing his fingers under the flange 242, and moves it towards the outer end of the chute member 204. The part 24 is accordingly caused to slide axially outwardly in a telescopic manner relative to the chute member 204. When the part 24 reaches the outer end the fingers are retained under the flange 242 and the bag and first coupling element are pressed in an axial direction using the thumbs of both hands, preferably placed approximately at opposite ends of the diameter, while the fingers remain under the flange 242 to absorb the reaction force. The resultant connected or coupled condition is seen in FIG. 3, from which it will be observed that the annular coupling part 12 is retained on the second coupling element due to the interengagement of the rims 122 and 246 and the engagement of rim 208 in recess 244. The seal strip 210 serves to minimize any leakage of liquids.

Bearing in mind that the peristomal area is normally very tender and sensitive, it is an important advantage of the invention that the telescopically slidable part 24 can be moved relative to the part 22, while the latter is attached to the wearer, without applying any tensile force to the area over which the medical grade adhesive pad is in contact with and sticking to the wearer. Avoidance of such tensile forces, as well as avoidance of applying compressive forces when applying pressure to couple the two coupling elements, is a valuable advantageous feature of the invention. Moreover, the security of attachment using this coupling system is in every important respect fully the equal of that obtained with the system according to British Patent No. 1 571 657 which has enjoyed wide commercial success.

As illustrated in full outline, the flange 242 is shown having a "cranked" shape at each side. As an optional alternative embodiment of the invention, this flange could be made (as shown at 243) to be a straight radial continuation of the portion 245 of the part 24. The straight flange extends radially outwardly from the remaining ring portion of the part 24 which contains recess 244 and rim 246.

It will be appreciated that modifications can be made without departing from the invention. For example, while use of a flexible strip 210 is considered preferable, other methods of achieving an adequate seal between the parts 12 and 22 may be employed. While the outwardly extending flange on the part 24 has been shown as a cranked flange 242 and alternatively as a straight and radially extending flange 243, other shapes or configurations may be employed. A significant advantage of the illustrated construction is that the body side coupling element 20 may be employed with any one of the many millions of standard bag side coupling elements 12 that are already in widespread use.

What is claimed is:

1. An ostomy coupling which includes a first channel shaped element for attaching to an ostomy bag and a second element for attaching to a pad of medical grade adhesive, each of these elements being of closed loop form and encircling a stomal orifice, in which the second element comprises a first part for attaching to the pad and a second part which is axially slidable relative to the first part for coupling the elements together and which second part has a radially outwardly extending flange under which the fingers can be placed when joining the elements to substantially prevent the application of pressure to the peristomal area, said second part being shaped so that when at the limit of its axial travel away from the pad, it cooperates with a stop on the first part to define a portion of the second coupling element shape chosen to be complementary to the first coupling element.

2. A coupling according to claim 1 in which the first part preferably includes a chute member for surrounding the stomal orifice.

3. A coupling according to claim 2 in which the chute member has a peripheral flexible seal strip located internally of the end of the chute which is remote from the pad and which is adapted to engage the outer side of the radially inner wall of the channel of the first element when the elements are coupled together.

4. A coupling according to claim 2 in which the chute member is substantially cylindrical in shape.

5. A coupling according to claim 4 in which the second part includes a ring portion and a flange portion extending radially outwardly therefrom.

6. The coupling according to claim 5 wherein the stop on the first part comprises a radially outwardly projecting rim on an end of the chute member and the second part comprises a recess on the end of the ring portion.

7. A coupling according to claim 6 in which the end of the ring portion of the second part comprises a radially outwardly extending rim interengaging an inwardly extending rim on the radially outer wall of said channel of said first element.

8. A coupling according to claim 7 wherein said flange portion on said second part is cranked to form a radially outer wall of a channel whose radially inner wall comprises said ring portion.

* * * * *